United States Patent [19]

Blank et al.

[11] Patent Number: 5,326,911
[45] Date of Patent: Jul. 5, 1994

[54] PROCESS FOR THE PREPARATION OF ORTHO-AMIDES

[75] Inventors: Heinz-Ulrich Blank, Odenthal; Helmut Kraus; Gerhard Marzolph, both of Cologne; Nikolaus Müller, Monheim, all of Fed. Rep. of Germany

[73] Assignee: Bayer Aktiengesellschaft, Leverkusen, Fed. Rep. of Germany

[21] Appl. No.: 916,922

[22] Filed: Jul. 20, 1992

[30] Foreign Application Priority Data

Jul. 30, 1991 [DE] Fed. Rep. of Germany ....... 4125159

[51] Int. Cl.$^5$ .................. C07C 209/06; C07C 209/14; C07C 209/22

[52] U.S. Cl. ..................... 564/468; 540/450; 540/605; 540/609; 544/162; 544/170; 544/332; 544/335; 544/336; 544/382; 546/248; 546/312; 548/193; 548/203; 548/206; 548/233; 548/245; 548/300.1; 548/326.5; 548/341.1; 548/356.1; 548/372.5; 548/376.1; 548/557; 548/562; 548/570; 549/68; 549/424; 549/480; 564/336; 564/346; 564/373; 564/374; 564/393; 564/394; 564/453; 564/455; 564/462; 564/504; 564/508

[58] Field of Search ..................... 564/468, 504, 508

[56] References Cited

U.S. PATENT DOCUMENTS

| | | | |
|---|---|---|---|
| 3,239,534 | 3/1966 | Winberg | 548/524 |
| 3,412,153 | 11/1968 | Bosshard et al. | 558/9 |
| 3,673,234 | 6/1972 | Ikawa et al. | 558/9 |
| 3,726,924 | 4/1973 | Leimgruber et al. | 564/474 |
| 3,922,285 | 11/1975 | Leimgruber et al. | 564/474 |
| 3,975,523 | 8/1976 | Hoffmann et al. | 558/198 |
| 4,958,026 | 9/1990 | Schoellkopf et al. | 548/304.4 |

FOREIGN PATENT DOCUMENTS

| | | |
|---|---|---|
| 598238 | 12/1960 | Belgium . |
| 1161285 | 7/1960 | Fed. Rep. of Germany . |
| 1205548 | 3/1962 | Fed. Rep. of Germany . |
| 1212069 | 7/1964 | Fed. Rep. of Germany . |
| 2023429 | 11/1970 | Fed. Rep. of Germany . |
| 2214497 | 10/1972 | Fed. Rep. of Germany . |
| 2215954 | 11/1972 | Fed. Rep. of Germany . |
| 94359 | 5/1971 | German Democratic Rep. . |

OTHER PUBLICATIONS

Bulletin de la Societe Chimique de France, No. 12, 1968, pp. 4985–4990.

(List continued on next page.)

*Primary Examiner*—Richard L. Raymond
*Assistant Examiner*—Scott C. Rand
*Attorney, Agent, or Firm*—Sprung, Horn, Kramer & Woods

[57] ABSTRACT

Ortho-amides of the formula

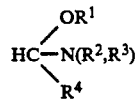

(I)

can be prepared by reacting salts of the formula

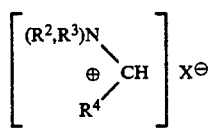

(II)

with alcoholates of the formula $M^1OR^1$ (III)

where the radicals $R^1$ to $R^4$, $M^1$ and $X^\ominus$ have the meaning given in the description. The alcoholates are employed in highly active form with an effective content of 98–100% $M^1OR^1$.

11 Claims, No Drawings

OTHER PUBLICATIONS

Chemische Berichte., vol. 104, No. 3, 1971 Weinheim de pp. 924–931.
Chemische Berichte., vol. 101, No. 1, 1968, Weinheim de pp. 41–50.
Helvetica Chimica Acta, 48, 1965, pp. 1746–1771.
Chem. Ber., 105, 1340–1344 (1972).
Angew. Chem. 72, 1969, pp. 836–845.
Chemical Abstracts, vol. 60, 9156–9157 (1964).
Chemical Abstracts, vol. 64, 19421, (1966).
Chemical Abstracts, vol. 64, 9593, (1966).
Chemical Abstracts, vol. 78, 469, (1973).
Rec. Trav. Chem. Pays-Bas 88, 1969, pp. 289–301.
Kantlehner et al., *Chem. Abs.* 77:4831j (1972).
Kurbanov et al., *Chem. Abs.* 102:78345K (1985).
Feugeas et al., *Chem. Abs.* 85:32379b (1976).

PROCESS FOR THE PREPARATION OF ORTHO-AMIDES

BACKGROUND OF THE INVENTION

1. Field of the Invention

The invention relates to the preparation of ortho-amides (alkoxy-aminomethanes), which include the two groups of the dialkoxy-dialkylaminomethanes (DMF acetals) and alkoxy-bis(dialkylamino)-methanes (aminal esters); to prepare them, highly active alcoholate suspensions are employed. DMF acetals and aminal esters are reactive $C_1$ units for the aminomethylenation of C-H-acidic compounds. These aminomethylenated substances represent valuable intermediates for the synthesis of heterocycles such as indoles, pyrimidines, pyridines and quinolonecarboxylic acids.

2. Description of the Related Art

To prepare ortho-amides, alkoxy groups can be replaced in a stepwise manner with amino groups on an acid catalyst by reaction of ortho-esters with secondary amines. However, the equilibrium is slanted towards the ortho-esters, a targeted exchange of one or two alkoxy groups is difficult, so that this method is mostly used for synthesising trisaminomethanes (DE-OS (German Published Specification) 2,214,497).

The use of chloroform instead of the ortho-esters (Rec. Trav. Chem. Pays-Bas 88 (1969), 289; DE-AS (German Published Specification) 1,161,285) has not proved to be very appropriate.

A selective preparation of DMF acetals and aminal esters is furthermore possible by reacting alkoxyiminomethylene salts or formamidiniumsalts with alcoholares (Chem. Bet. 101 (1968), 41). The yields in the case of five different aminal esters are between 62 and 72%, and in the case of one aminal ester 79%; in the case of 14 different amide acetals they are between 42 and 63%, while DMF dimethyl acetal is said to be obtainable in 75-87% of the theoretical yield. However, DMF dimethyl acetal is reported, in DD 94,359, to be obtainable in not more than 50-55% by this process because of decomposition. According to the description in Helv. Chim. Acta 48 (1965), 1746, this method gives the DMF dimethyl acetal in a yield of only 37% of the theoretical yield.

DE-AS (German Published Specification) 1,205,548 describes the preparation of a range of aminal esters. Yields of 62-77% are obtained using a 10% excess of expensive, alcohol-free alcoholate. It was impossible to confirm the statement that, starting from raw formamidinium salt which contains one equivalent of methanol for production reasons, the methyl aminal ester is obtained in 68% of the theoretical yield. When the synthesis was reproduced, the result was a 1.8:1 amide acetal/aminal ester mixture in 65% of the theoretical yield.

Following U.S. Pat. No. 3,239,534 and without using a solvent, 19.1% of the theoretical yield of DMF acetal was obtained from dimethylformamide, dimethyl sulphate and alcoholate, and 25.6% of aminal ester with the additional use of dimethylamine.

The reaction of bis (dialkylamino)-acetonitriles with alcoholares (Chem. Bet. 105 (1972), 1340) is described as an elegant, homogeneously proceeding reaction. The yields of aminal esters are around 76-84%, however, the preparation of the acetonitriles used is only possible in 53% of the theoretical yield starting from the formamidinium salts (Chem. Ber. 104 (1971), 924).

Synthesis of DMF acetal is also possible by reacting two equivalents of alcoholate with amide chlorides (Angew. Chem. 72 (1969), 836; BE 598,238). However, when they are prepared from dialkylformamides using chlorinating agents such as $POCl_3$, $SOCl_2$ and others, the carcinogenic carbamide chlorides are always formed as by-products.

Besides the varying yields of 40-75%, which are relatively low for industrial syntheses, working-up as is known from the literature is not suitable for an industrial process. If, after the reaction to give the orthoamide, first the solvent and then the desired product is removed from the salt residue by distillation, the result is, according to DD 94,359, decomposition reactions and yield losses. This is why this Patent Specification attempts to increase the yield to 85% by entraining the product using methanol. However, this process entails large amounts of solvent to be distilled twice. Furthermore, separation of methanol and DMF dimethyl acetal by distillation is difficult. Moreover, when the synthesis was reproduced, the high yield indicated could not be obtained.

The previous removal of the salts is also problematic. On the one hand, methylsulphates are partially soluble in polar media such as, for example, alcohols, on the other hand, they are obtained in gel-like, lumpy or very finely crystalline form, depending on solvent and how the reaction is carried out, which makes filtration very difficult.

Aqueous working-up is impossible because of the sensitivity of the ortho-amides to hydrolysis.

SUMMARY OF THE INVENTION

Surprisingly, a process for the preparation of amide acetals and aminal esters has now been found, which avoids these known difficulties and yields the orthoamides in high, reproducible yields. In this process according to the invention, an alcoholate in a highly reactive form is employed as a suspension, since it has been shown, that it is not sufficient to bring the alcoholate into an alcohol-free form.

The invention therefore relates to a process for the preparation of ortho-amides of the formula

in which $R^1$ denotes straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_2$–$C_8$-alkylene-$OM^1$ or $C_7$–$C_{10}$-aralkyl, $R^2$ and $R^3$, independently of one another, represent straight-chain or branched $C_1$–$C_8$-alkyl, $C_2$–$C_8$-alkenyl, $C_2$–$C_8$-alkoxyalkyl, $C_3$–$C_8$-alkoxyalkenyl, $C_3$–$C_8$-cycloalkyl, $C_6$–$C_{12}$-aryl, $C_7$–$C_{10}$-aralkyl, or a 5- to 8-membered saturated or unsaturated heterocyclic ring whose hetero atoms 1 or 2 are from the group comprising N, O and S, where furthermore $R^2$ and $R^3$, together with the N atom which they substitute, can form a 5- to 8-membered ring which can contain a further hetero atom from the group comprising N, O and S, and R[4] represents —OR[5] or —N(R[5],R[6]) in which R[5] and R[6], independently of one another and independently of R[2] and R[3], have the range of meanings mentioned in the case of R[2] and R[3], which is characterised in that salts of the formula

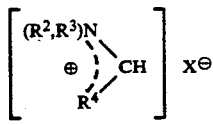 (II)

in which

R[2], R[3] and R[4] have the abovementioned meaning and X$^\ominus$ denotes the $C_1$–$C_8$-alkylsulphate anion, the $C_6$–$C_{12}$-arylsulphonate anion, the tetrafluoroboranate anion, the $C_6$–$C_{12}$-arylsulphate anion, the chloride anion, the bromide anion, the iodide anion, the hexafluorophosphate anion, the $C_1$–$C_8$-alkylsulphonate anion, the $C_1$–$C_8$-halogenoalkylsulphonate anion, the $C_1$–$C_8$-halogenoalkylsulphate anion, the perchlorate anion or the hexachloroantimonate anion, are reacted in the presence of alcoholares of the formula $M^1OR^1$ (III)

in which

R[1] has the range of meanings mentioned and

M[1] is an equivalent of an alkali metal cation or alkaline earth metal cation, the alcoholate being employed in highly active form.

Straight-chain or branched $C_1$–$C_8$-alkyl is, for example, methyl, ethyl, propyl, isopropyl, butyl, isobutyl, tert-butyl and the amyl, hexyl and octyl isomers, preferably the $C_1$–$C_4$-alkyl radicals mentioned.

$C_2$–$C_8$-Alkenyl is vinyl, propenyl, allyl and the butenyl, amylenyl hexenyl or octenyl isomers preferably the $C_3$–$C_4$-alkenyl radicals mentioned

$C_2$–$C_8$-Alkoxyalkyl is, for example, methoxymethyl, ethoxymethyl, methoxyethyl as well as further radicals from the $C_3$–$C_9$-alkyl group in which a $CH_2$ group is replaced by an O atom.

$C_3$–$C_8$-Alkoxyalkenyl is, for example, methoxyvinyl, ethoxyvinyl, methoxyallyl, 2-methoxy-propenyl and others from the group of $C_4$–$C_9$-alkenyl radicals in which a $CH_2$ group is replaced by an O atom.

$C_3$–$C_8$-Cycloalkyl is, for example, cyclopropyl, methylcyclopropyl, dimethyl-cyclopropyl, cyclobutyl, methylcyclobutyl, dimethyl-cyclobutyl, cyclopentyl, methyl-cyclopentyl, cyclohexyl, methyl-cyclohexyl, dimethyl-cyclohexyl, cycloheptyl, cyclooctyl, preferably cyclopropyl, cyclopentyl and cyclohexyl, and their methyl or dimethyl derivatives.

$C_6$–$C_{12}$-Aryl is, for example, phenyl, naphthyl or biphenylyl, preferably phenyl.

$C_7$–$C_{10}$-Aralkyl is, for example, benzyl, 1-phenylethyl, 2-phenylethyl and further radicals of this type which are known to a person skilled in the art, preferably benzyl.

The following may be mentioned as a 5- to 8-membered saturated or unsaturated heterocyclic ring whose hetero atoms 1 or 2 are from the group comprising N, O and S: pyrrole, furan, thiophene, pyrrolidine, pyrazole, imidazole, thiazole, oxazole, pyridine, pyrimidine, piperazine, morpholine, pyran, azepine, azocine, isoxazole, isothiazole, pyridazine and pyrazine. It is known to a person skilled in the art that unsaturated heterocyclic rings can have a more or less pronounced aromatic character.

Furthermore, R[2] and R[3], together with the N atom which they substitute, can form a 5- to 8-membered saturated or unsaturated ring which can contain a further hetero atom from the group comprising N, O and S. Examples of such systems are pyrrole, pyrrolidine, pyrroline, pyrazole, pyrazolidine, imidazole, imidazolidine, thiazole, thiazolidine, piperazine, piperidine, morpholine, azepine and dihydroazocine.

In the event that R[1] represents $C_2$–$C_8$-alkylene-OM[1], (III) is the alcoholate of a diol having 2 to 8 C atoms, such as glycol, 1,2-propanediol, 1,3-propanediol, 1,2-, 1,3- or 1,4-butanediol, hexanediol or octanediol.

The $C_1$–$C_8$-alkylsulphate anion is, for example, the anion of methylsulphuric acid, ethylsulphuric acid, propylsulphuric acid, isopropylsulphuric acid, butylsulphuric acid, isobutylsulphuric acid, one of the hexylsulphuric acid isomers or octylsulphuric acid isomers.

The $C_1$–$C_8$-alkylsulphonate anion or the $C_1$–$C_8$-halogenoalkylsulphonate anion is, for example, the anion of methylsulphonic acid, trichloromethylsulphonic acid, trifluoromethylsulphonic acid or sulphonic acid having a higher (halogeno) alkyl radical.

The $C_6$–$C_{12}$-arylsulphonate anion is, for example, the anion of benzenesulphonic acid, naphthalenesulphonic acid, biphenyl-sulphonic acid, toluenesulphonic acid, preferably of benzenesulphonic acid or toluenesulphonic acid.

The $C_6$–$C_{12}$-arylsulphate anion is, for example, the anion of phenylsulphuric acid, of naphthylsulphuric acid or of biphenylsulphuric acid.

X$^\ominus$ is preferably halide or alkylsulphate, particularly preferably chloride or methylsulphate.

M[1] is an equivalent of an alkali metal cation or alkaline earth metal cation, for example the cation of lithium, sodium, potassium, rubidium, caesium, magnesium, calcium, strontium, barium; preferably the cation of an alkali metal, particularly preferably the cation of sodium or potassium.

Salts coming under those which are used for the reaction according to the invention are both alkoxymethyleneiminium salts as well as formamidinium salts of the formulae

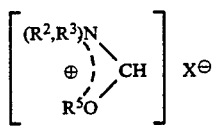 (IIa)

or

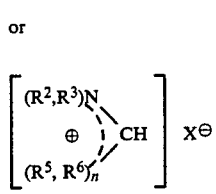 (IIb)

The reaction of the process according to the invention can, for example, be represented by way of formulae as follows:

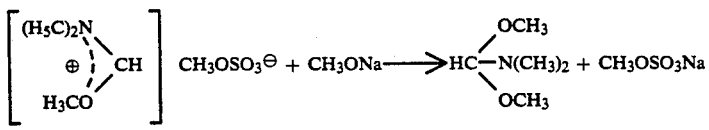

or

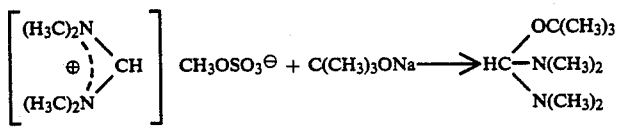

In the event that $R^1$ and $R^5$ are not identical, an acetal of the formula (I), in which $R^4$ is therefore $OR^5$, will exist as a mixture of the three acetals which are possible ($R^1,R^1$; $R^1,R^5$; $R^5,R^5$). One of the pure acetals can be obtained from such a mixture by transacetalisation.

In a preferred manner, a salt of the formula

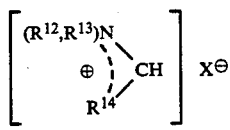 (IV)

is reacted, in which
$R^{12}$ and $R^{13}$, independently of one another, denote straight-chain or branched $C_1$-$C_8$-alkyl, cyclopropyl, cyclopentyl, cyclohexyl, phenyl or benzyl and $R^{12}$ and $R^{13}$ furthermore, together with the N atom which they substitute, can form a 5- to 8-membered saturated or unsaturated N-heterocyclic ring which can contain a further hetero atom from the group comprising N, O and S,
$R^{14}$ represents $-OR^{12}$ or $-N(R^{12},R^{13})$ and
$X^\ominus$ assumes the above meaning.

In a particularly preferred manner, salts of the formula

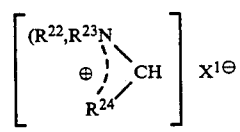 (V)

are reacted, in which
$R^{22}$ and $R^{23}$, independently of one another, denote straight-chain or branched $C_1$-$C_4$-alkyl and $R^{22}$ and $R^{23}$ furthermore, together with the N atom which they substitute, can denote morpholino, pyrrolidino or piperidino,
$R^{24}$ represents $-OR^{22}$ or $-N(R^{22},R^{23})$ and
$X^{1\ominus}$ denotes the $C_1$-$C_8$-alkylsulphate anion, the chloride anion, the bromide anion or the iodide anion.

In a very particularly preferred manner, the radicals $R^5$ and $R^6$ are identical with the radicals $R^2$ and $R^3$. In a furthermore very particularly preferred manner, the substituents $R^2$, $R^3$, $R^5$ and $R^6$ represent the methyl radical or ethyl radical. In a furthermore preferred manner, $X^{1\ominus}$ represents the chloride ion or the $C_1$-$C_4$-sulphate anion, very particularly preferably the methylsulphate anion.

The process according to the invention is furthermore particularly important for salts of the formula

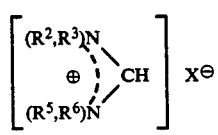 (VI)

preferably salts of the formula

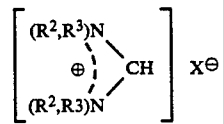 (VII)

in which
$R^2$, $R^3$, $R^5$, $R^6$ and $X^\ominus$ have the abovementioned meaning.

In a furthermore preferred manner, the reaction is carried out with an alcoholate of the formula $$M^2OR^{11} \qquad (VIII)$$

in which
$R^{11}$ represents straight-chain or branched $C_1$-$C_5$-alkyl, $C_2$-$C_5$-alkoxyalkyl or $C_2$-$C_4$-alkylene-$OM^2$ and
$M^2$ denotes $Na^\ominus$ or $K^\ominus$.

In a further particularly preferred manner, the reaction is carried out with an alcoholate of the formula $$M^2OR^{21} \qquad (IX)$$

in which
$R^{21}$ represents straight-chain or branched $C_1$-$C_5$-alkyl and
$M^2$ denotes $Na^\ominus$ or $K^\ominus$.

Solvents which can be employed for the process according to the invention are inert solvents such as (halogeno)hydrocarbons, ethers and others, which preferably have an increased boiling point and which are listed individually further below.

It is a particular feature of the invention that a highly active alcoholate is employed. This is because it has been shown that an alcoholate which had been removed from a freshly opened delivery container only gives unsatisfactory results. An alcoholate which had been stripped of its remaining alcohol, especially alcohol of crystallisation, by additional drying or by brief dry incipient distillation, also gave no substantially improved results. However, it has been shown, surprisingly, that a finely-divided alcoholate which had been obtained from a solution, for example an alcoholic solution, in the absence of water, $CO_2$ and other substances which react with alcoholate, shows such a high degree of activation that the yield is improved dramatically. This high level of activation is in agreement with the hypothesis that alcoholares of the abovementioned origin have a superficial hydroxide or carbonate/hydrogen carbonate crust which disturb the heterogeneous reaction greatly.

Highly active alcoholates which can be used according to the invention are furthermore obtained by spray-drying of an alcoholate solution in a pure atmosphere of $N_2$. The preferred route for preparing a highly active alcoholate, however, consists in heating the alcoholate which is dissolved in an alcohol in a non-solvent at a temperature above the temperature at which the alcohol of crystallisation is eliminated. For this purpose, this non-solvent must have a boiling point which is sufficiently above the temperature of elimination, which can also be achieved by applying a pressure. However, for reasons of simpler processibility, non-solvents will be used whose boiling point is above 120° C., preferably above 130° C., even under atmospheric pressure. The alcohol and alcohol of crystallisation to be separated off are subsequently removed from such a heated mixture by fractional distillation or distillation in the form of a mixture or azeotrope together with the high-boiling non-solvent employed. Particularly suitable non-solvents for this purpose are: inert, preferably high-boiling liquids such as straight-chain or branched higher hydrocarbons of the aliphatic, aromatic or araliphatic series, for example decane, isododecane, biphenyl, xylene, naphthalene, triisopropylbenzene, diphenylmethane, technical-grade mixtures of benzylated benzenes, such as the heat transfer oil Marlotherm S or Autin B, furthermore technical-grade mineral oil mixtures; furthermore halogen compounds such as ethers, nitro compounds, nitriles, such as dichlorobenzene, diphenyl ether, ditolyl ether, nitrobenzene and benzonitrile; finally inorganic/organic liquids such as silicone oil. Under superatmospheric pressure, liquids which would usually boil at lower temperatures are also suitable, such as toluene, cyclohexane, petroleum ether, dioxane, tetrahydrofuran, dibutyl ether and others.

Such highly active alcoholates which can be used according to the invention have the additional, but not decisive, effect that they are substantially free from alcohol and, accordingly, have a high effective content (98 to 100% $M^1OR^1$).

The surprising advantage of the process according to the invention becomes clear when, compared with the use according to the invention of an alcoholate in substantially alcohol-free form, a different, technically available, solid alcoholate powder is employed, which has an effective content in the range of approximately 90-97%. Even when the process is carried out under otherwise identical conditions, i.e. also in a suspension of such a technical-grade alcoholate powder in a comparable, higher-boiling solvent, only yields of 60-70% of the theoretical yield are obtained.

Surprisingly, a yield of desired ortho-amide is obtained according to the invention which is up to 50% higher.

The preferred variant of the preparation of a substantially alcohol-free alcoholate by treating a technical-grade alcoholate in a high-boiling solvent and carrying out the reaction of the process according to the invention in the resulting suspension of the alcoholate in this solvent also means that handling pulverulent alcoholate, which is dusty, corrosive and self-igniting in the air, is avoided. Moreover, this form of handling allows the use of technically available alcoholate solutions in alcohol as starting materials as they are obtained during the preparation of such an alcoholate. This advantage applies, in particular, to the lower $C_1$-$C_5$-alcoholates, and, very particularly, to the use of methylate.

The process according to the invention can be carried out in such a way that the alkoxymethyleneiminium salt or formamidinium salt is melted, the melt is dissolved or suspended in a solvent, and metered into the alcoholate suspension at a temperature of 0°-80° C., preferably 20°-60° C. Addition in the reverse order is also possible. The ratio of salt:alcoholate is in the range of 1.5:1–1:1.5, preferably in the range of 1.2:1–1:1.2. Stirring is continued for a short time, and the reaction has then ended. Workingup is expedient when one of the abovementioned inert, high-boiling solvents or a mixture of a plurality of these is used. For example, the desired ortho-amides are obtained in pure form by distillating off from the reaction mixture in which the resulting salt exists in suspended form.

By simple diluting the distillation residue with water followed by phase separation, the non-polar, high-boiling solvent is recycled virtually completely and can be re-employed after brief incipient distillation in order to remove the water present.

The desired ortho-amides are obtained in pure form (purity above 95%, in most cases above 97%). The pure form is also understood as meaning the dismutation mixture of the ortho-amides, specifically, of the aminal esters, which can be obtained in a ratio of amide acetal::aminal ester:trisdialkylaminomethane=0:1:0 to 0.33:0.34:0.33. However, since in further reactions, specifically with aminal esters, the dismutation proceeds at a faster rate than this further reaction, it is immaterial which dismutation mixture is obtained according to the invention as the reaction product and then employed in such further reactions.

EXAMPLES (all operations were carried out under protective gas)

Example 1

180 g of 30% strength methanolic sodium methylate solution and 250 ml of triisopropylbenzene were initially introduced and heated; methanol was distilled off until the bottom temperature had reached 140° C. At 40° C. 221 g of 96.1% tetramethylformamidinium methylsulphate were added dropwise (contained 1.1% DMF and 2.8% salt of dimethylamine and methylsulphuric acid). After the mixture had been stirred for 20 minutes, the product mixture was distilled off using a Vigreux column. This gave 128 g of 97.1% methyl aminal ester (2.8% DMF; 0.1% triisopropylbenzene), 15% of which had been dismutated, corresponding to 94.1% of theory. The distillation residue was treated with water. After phase separation, the organic solvent was subjected to incipient distillation to remove water, and used for further reactions.

Example 2

A suspension was prepared analogously to Example 1 with 324 g of 21% strength ethanolic sodium ethylate solution and 250 ml of triisopropylbenzene. At 40° C., 221 g of 96.1% tetramethylformamidinium methylsulphate were added dropwise. 138 g of 97.6% ethyl aminal ester (remainder DMF) were obtained after distillation (92.3% of theory).

Example 3

274 g of a 35% strength sodium tert-butylate solution in tetrahydrofuran were treated with 300 ml of mineral oil, and the ether was removed by distillation At 35° C., 230 g of 96.1% tetramethylformamidinium methylsulphate were added dropwise. 163.8 g of 96.7% t-butyl aminal ester were obtained after distillation in the form of a 0.24:0.48:0.28 dismutation mixture.

Example 4

55 g of a melt of 35% sodium isobutylate and 65% isobutanol were treated with 100 ml of mineral oil, and the alcohol was removed by distillation. At 50° C., 44.6 g of 95% tetramethylformamidinium methylsulphate were added dropwise, and isobutyl aminal ester was obtained after the distillation in the form of a dismutation mixture, yielding 90.9% of theory.

Example 5

Half of the alcohol in 370 g of potassium tert-pentylate solution, obtained by dissolving 0.5 mol of potassium in 4 mol of t-pentanol, were distilled off immediately and the remainder after addition of 120 ml of ditolyl ether. At 37° C., 110 g of 96% tetramethylformamidinium methylsulphate were added dropwise, and the product was distilled in vacuo. This gave 91.3% of theory of t-pentyl aminal ester.

Example 6

203 g of 97.1% methoxymethyleneiminium methylsulphate (contained 0.7% of dimethyl sulphate and 2.2% of DMF) were added dropwise at room temperature to a sodium methylate suspension described in Example 1. After the mixture had been stirred for 30 minutes, the product was distilled off. This gave 98.4% DMF acetal, yielding 92.4% of theory (contained 0.9% of methanol; 0.7% of DMF).

Example 7

Analogously to Example 6, isododecane was used instead of triisopropylbenzene. This gave DMF acetal, yielding 90.4% of theory.

COMPARISON EXAMPLES

Comparison Example 1

180 g of 30% strength methanolic sodium methylate solution were treated with 200 ml of dry methanol. 205 g of 91.1% methoxymethyleneiminium methylsulphate were added dropwise with ice-cooling. After the mixture had been stirred for 1 hour, the salt was filtered off with the aid of a protective gas frit, and the filtrate was distilled over a Vigreux column. This gave 68.3 g of 96.3% DMF acetal (remainder methanol, traces of DMF).

Comparison Example 2

227 g of 21% strength sodium methylate solution were evaporated to dryness and treated with 250 ml of dried methyl tert-butyl ether: 148.4 g of 97.4% tetramethyl-formamidinium methylsulphate were added dropwise at 40° C. After the mixture had been stirred for 1 hour at room temperature, the mixture was filtered over a protective gas frit and rinsed with 50 ml of dry cyclohexane. $^1$H NMR spectroscopic analysis of the filtrate showed the presence of ethyl aminal ester (in the form of a dismutation mixture), yielding 51.1% of theory.

Comparison Example 3

36.6 g of sodium ethylate powder from a freshly opened container were introduced into 300 ml of isododecane. 108.6 g of 97.6% tetramethylformamidinium methylsulphate were added dropwise at 40° C., and stirring was continued for 4 hours at room temperature. All volatile components were condensed in a cold trap up to 50° C./2 mbar. The distillate contained 44.0% dismutated ethyl aminal ester, corresponding to 65.0% of theory.

Comparison Example 4

37.4 g of technical-grade sodium ethylate powder (90.9%) were introduced into 250 ml of triisopropylbenzene. The mixture was heated to 140° C., and 30 ml of solvent were distilled off by reducing the pressure to 100 mbar. 108.6 g of 97.6% tetramethylformamidinium methylsulphate were subsequently added dropwise at 40° C. and the mixture was worked up analogously to Comparison Example 3. This gave dismutated ethyl aminal ester, yielding 68.3% of theory.

What is claimed is:

1. A process for the preparation of an ortho-amide of the formula

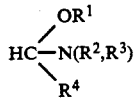

in which
R$^1$ denotes straight-chain or branched C$_1$–C$_8$-alkyl, C$_2$–C$_8$-alkenyl, C$_2$–C$_8$-alkoxyalkyl, C$_3$–C$_8$-alkoxyalkenyl, C$_3$–C$_8$-cycloalkyl, C$_2$–C$_8$-alkylene-OM$^1$ or C$_7$–C$_{10}$-aralkyl, R$^2$ and R$^3$, independently of one another, represent straight-chain or branched C$_1$–C$_8$-alkyl, C$_2$–C$_8$-alkenyl, C$_2$–C$_8$-alkoxyalkyl, C$_3$–C$_8$-alkoxyalkenyl, C$_3$–C$_8$-cycloalkyl, C$_6$–C$_{12}$-aryl, C$_7$–C$_{10}$-aralkyl, or a 5- to 8-membered saturated or unsaturated heterocyclic ring containing 1 or 2 hetero atoms selected from the group consisting of N, O and S, or R$^2$ and R$^3$, together with the N atom which they substitute, form a 5- to 8-membered ring which can contain a further hetero atom selected from the group consisting of N, O and S, and R$^4$ represents —OR$^5$ or —N(R$^5$,R$^6$) in which R$^5$ and R$^6$, independently of one another and independently of R$^2$ and R$^3$, have the range of meanings mentioned in the case of R$^2$ and R$^3$, which comprises maintaining an alcohol solution of an alcoholate of the formula

in which
M$^1$ is an equivalent of an alkali metal cation or alkaline earth metal cation, at a temperature of 120° to 200° C. in a high boiling non-solvent selected from the group consisting of a hydrocarbon, a halogenated, nitro, or cyano hydrocarbon, an ether and a silicon oil, distilling off the entire alcohol and alcohol of crystallization, thereby to place the alcoholate in highly active form, and reacting such highly active alcoholate with a salt of the formula

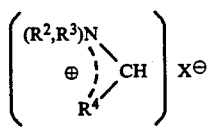

in which

X$^\ominus$ is a $C_1$–$C_8$-alkylsulphate, $C_6$–$C_{12}$-arylsulphonate, tetrafluoroboranate, $C_6$–$C_{12}$-arylsulphate, chloride, bromide, iodide, hexafluorophosphate, $C_1$–$C_8$-alkylsulphonate, $C_1$–$C_8$-halogenoalkylsulphonate, $C_1$–$C_8$-halogenoalkylsulphate, perchlorate or hexachloroantimonate anion.

2. The process of claim 1, wherein a salt of the formula

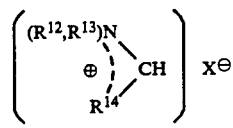

is reacted, in which $R^{12}$ and $R^{13}$, independently of one another, denote straight-chain or branched $C_1$–$C_8$-alkyl, cyclopropyl, cyclopentyl, cyclohexyl, phenyl or benzyl, or $R^{12}$ and $R^{13}$, together with the N atom which they substitute, form a 5- to 8-membered saturated or unsaturated N-heterocyclic ring which can contain a further hetero atom selected from the group consisting of N, O and S, $R^{14}$ represents —$OR^{12}$ or —$N(R^{12},R^{13})$ and X$^\ominus$ denotes the $C_1$–$C_8$-alkylsulphate anion, the $C_6$–$C_{12}$-arylsulphonate anion, the tetrafluoroboranate anion, the $C_6$–$C_{12}$-arylsulphate anion, the chloride anion, the bromide anion, the iodide anion, the hexafluorophosphate anion, the $C_1$–$C_8$-alkylsulphonate anion, the $C_1$–$C_8$-halogenoalkylsulphonate anion, the $C_1$–$C_8$-halogenoalkylsulphate anion, the perchlorate anion or the hexachloroantimonate anion.

3. The process of claim 2, wherein a salt of the formula

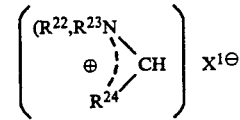

in reacted, in which $R^{22}$ and $R^{23}$, independently of one another, denote straight-chain or branched $C_1$–$C_4$-alkyl, or $R^{22}$ and $R^{23}$, together with the N atom which they substitute, denote morpholino, pyrrolidino or piperidino, $R^{24}$ represents —$OR^{22}$ or —$N(R^{22},R^{23})$ and $X^{1\ominus}$ is a $C_1$–$C_8$-alkylsulphate, chloride, bromide or iodine anion.

4. The process of claim 1, wherein a salt of the formula

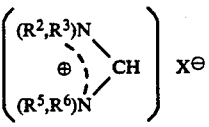

is employed.

5. The process of claim 4, wherein a salt of the formula

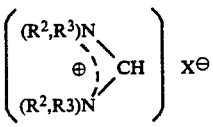

is employed.

6. The process of claim 1, which is carried out in the presence of an alcoholate of the formula $$M^2OR^{11}$$

in which $R^{11}$ represents straight-chain or branched $C^1$–$C^5$-alkyl, $C_2$–$C_5$-alkoxyalkyl or $C_2$–$C_4$-alkylene-$OM^2$ and $M^2$ denotes the sodium or potassium cation.

7. The process of claim 6, which is carried out in the presence of an alcoholate of the formula $$M^2OR^{21}$$

in which $R^{21}$ represents straight-chain or branched $C_1$–$C_5$-alkyl and $M^2$ denotes the sodium or potassium cation.

8. The process of claim 1, wherein the alcoholate is methylate.

9. The process of claim 1, wherein the alcoholate is treated at a temperature of 130° to 180° C.

10. The process of claim 1, wherein the ratio of salt:alcoholate is from 1.5:1 to 1:1.5.

11. The process of claim 10, wherein the ratio of salt:alcoholate is from 1.2:1 to 1:1.2.

* * * * *

UNITED STATES PATENT AND TRADEMARK OFFICE
CERTIFICATE OF CORRECTION

PATENT NO : 5,326,911
DATED : July 5, 1994
INVENTOR(S): Heinz-Ulrich Blank, et al.

It is certified that error appears in the above-identified patent and that said Letters Patent are hereby corrected as shown below:

Column 12, line 35, cancel "$C^1$-$C^5$" and substitute --$C_1$-$C_5$--.

Signed and Sealed this

Twenty-first Day of September, 1999

Attest:

Q. TODD DICKINSON

*Attesting Officer*     *Acting Commissioner of Patents and Trademarks*